(12) United States Patent
Hirasawa et al.

(10) Patent No.: US 10,166,409 B2
(45) Date of Patent: Jan. 1, 2019

(54) FLUOROSCOPIC DEVICE, MOVING BODY TRACKING DEVICE FOR RADIATION THERAPY, AND X-RAY DETECTOR

(71) Applicant: SHIMADZU CORPORATION, Kyoto (JP)

(72) Inventors: Shinya Hirasawa, Kyoto (JP); Tatsuya Araki, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 190 days.

(21) Appl. No.: 15/327,925

(22) PCT Filed: Sep. 22, 2014

(86) PCT No.: PCT/JP2014/074991
§ 371 (c)(1),
(2) Date: Jan. 20, 2017

(87) PCT Pub. No.: WO2016/046870
PCT Pub. Date: Mar. 31, 2016

(65) Prior Publication Data
US 2017/0197098 A1    Jul. 13, 2017

(51) Int. Cl.
*A61B 6/00* (2006.01)
*A61N 5/10* (2006.01)

(52) U.S. Cl.
CPC .............. *A61N 5/1077* (2013.01); *A61B 6/00* (2013.01); *A61B 6/42* (2013.01); *A61B 6/461* (2013.01); *A61B 6/487* (2013.01); *A61N 5/1049* (2013.01); *A61N 2005/1061* (2013.01); *A61N 2005/1089* (2013.01)

(58) Field of Classification Search
CPC ....................................................... A61B 6/487
See application file for complete search history.

(56) References Cited

U.S. PATENT DOCUMENTS

2009/0175418 A1* 7/2009 Sakurai ............... A61N 5/1048
378/98.5
2014/0018604 A1* 1/2014 Ishikawa ............. A61B 6/4452
600/1

FOREIGN PATENT DOCUMENTS

JP        3053389       6/2000
JP        2006-21046    1/2006

OTHER PUBLICATIONS

PCT/JP2014/074991, ISR dated Jan. 13, 2015, 1 page—English, 2 pages—Japanese; Written Opinion—1 page—English, 5 pages—Japanese.

* cited by examiner

*Primary Examiner* — Dani Fox
(74) *Attorney, Agent, or Firm* — Andrew F. Young, Esq.; Lackenbach Siegel, LLP

(57) ABSTRACT

An X-ray fluoroscopic device includes an X-ray imaging mechanism having an X-ray tube 1 and a flat panel detector 2; filters 23 to form a correction region, in which the scattered radiation S caused by irradiating the therapeutic beam to the subject 57 can be incident, but the X-ray that is irradiated from the X-ray tube 1 and transmits through the subject 57 cannot be incident; and a correction element that corrects the data of the region other than the correction region of the flat panel detector 2 by using the data of the correction region of the flat panel detector 2.

8 Claims, 14 Drawing Sheets

FLUOROSCOPIC DEVICE, MOVING BODY TRACKING DEVICE FOR RADIATION THERAPY, AND X-RAY DETECTOR

CROSS REFERENCE TO RELATED APPLICATIONS

This application relates to and claims priority from PCT Ser. No.:PCT/JP2014/074991 filed Sep. 22, 2014, the entire contents of which are incorporated herein by reference.

FIGURE SELECTED FOR PUBLICATION

FIG. 4

BACKGROUND OF THE INVENTION

Field of the Invention

The present invention relates to an X-ray fluoroscopic device to be used relative to a radiation therapy apparatus for performing a radiation therapy by irradiating a therapy beam to a subject, a dynamic (moving) body tracking device and an X-ray detector.

Description of the Related Art

A radiation must be irradiated exactly to an affected region relative to the radiation therapy apparatus, having a head that irradiates the therapeutic beam and a gantry to rotate the head around a subject as the center, that performs a radiation therapy by irradiating the therapeutic beam, including e.g., X-ray and an electron beam and so forth to the affected region such as a tumor and so forth. Nevertheless, in some cases, not only the subject unintentionally may move the body thereof, but also the affected area per se may move. For example, a tumor near the lung largely moves depending on breathing. Accordingly, a radiation therapeutic device comprising a mechanism, in which the X-ray fluoroscopic device detects the position of a metal marker in-place near the tumor and then the therapeutic radiation to be irradiated is controlled thereby, is disclosed (referring to Patent Document 1).

As such radiation therapy apparatus, an X-ray fluoroscopy apparatus that identifies the location of the marker by fluoroscoping the image including the marker implanted inside the body of the subject. According to such X-ray fluoroscopy device, an implanted marker inside body by a template matching and so forth by using a first fluoroscopic mechanism including a first X-ray tube that irradiates an X-ray from the floor surface side and a first X-ray detector that detects the X-ray passing through the subject from the ceiling side and a second fluoroscopic mechanism including a second X-ray tube that irradiate an X-ray from the floor surface side and a second X-ray detector that detects the X-ray passing through the subject from the ceiling side. And 3-dimensional positional data can be acquired by utilizing a 2-dimensional fluoroscopy image imaged by the first fluoroscopic mechanism and a 2-dimensional fluoroscopy image imaged by the second fluoroscopic mechanism. Accordingly, the dynamic tracking to detect the moving maker of the region with a high degree of accuracy can be performed by continuously performing such operations and calculating the real-time 3-dimensional positional data. And an irradiation of the therapeutic radiation is controlled based on the positional data of the marker acquired by such dynamic body tracking so that the irradiation of the radiation corresponding to such move of the tumor can be performed with a high degree of accuracy.

FIG. 12 is a schematic view illustrating the state in which a radiation therapy is being conducted by a radiation therapeutic device having a traditional fluoroscopy apparatus.

The present radiation therapeutic apparatus is to provide a therapeutic treatment by irradiating an X-ray or an electron beam to the affected area of the subject 57 lying on the table 56 and comprises a head 55 in order to irradiate the therapeutic beam B toward the subject 57. In addition, such radiation therapeutic apparatus comprises a first X-ray fluoroscopic mechanism consisting of the first X-ray tube 1a and the first X-ray detector 2a and a second X-ray fluoroscopic mechanism consisting of the second X-ray tube 1b and the second X-ray detector 2b so that fluoroscopy an image including the marker inside the subject 57 in order to perform a dynamic body tracking can be performed.

According to the aspect of such radiation therapy apparatus, the therapeutic beam B that is irradiated from the head 55 to the subject 57 becomes scattered radiation S and then is incident into the first X-ray detector 2a and the second X-ray detector 2b. When such scattered radiation S is incident into the first X-ray detector 2a and the second X-ray detector 2b, an artifact takes place in the image imaged by the first X-ray detector 2a and the second X-ray detector 2b, so that it is problematic that the dynamic body tracking can be interrupted.

Therefore, according to the aspect of an radiation therapy apparatus disclosed in Patent Document 1, an irradiation of the therapeutic beam B and an irradiation of the X-ray for dynamic body tracking are synchronized and the gate of the image intensifier (I. I.) is turned on except the irritation of the X-ray to perform the dynamic body tracking by utilizing a function of the image intensifier as the X-ray detector so that the scattered radiation S due to the therapeutic beam B cannot be received and the irradiation of the therapeutic beam B can be suspended when the X-ray is irradiated.

RELATED PRIOR ART DOCUMENTS

Patent Document

Patent Document 1: JP Patent 3053389 B1

ASPECTS AND SUMMARY OF THE INVENTION

Problems to be Solved by the Invention

FIG. 13 is a timing chart illustrating indicating the state of the therapeutic beam B and the irradiation of e.g., X-ray for dynamic body tracking and so forth when the image intensifier (I. I.) is used as an X-ray detector. Referring to FIG. 13, the sign B indicates ON-and-OFF of the therapeutic beam B, the sign X indicates ON-and-OFF of the X-ray for dynamic body tracking and the sign G indicates On-and-Off of the gate of the image intensifier.

Referring to FIG. 13, according to the aspect of the radiation therapy apparatus disclosed in Patent Document 1 described above, the gate of the image intensifier is turned on while irradiating the therapeutic beam B so that the image intensifier cannot detect the scattered radiation S due to the therapeutic beam. And the image intensifier is turned off while irradiating the X-ray for dynamic body tracking to detect the X-ray and the irradiation of the therapeutic beam B is suspended as indicated by the broken line in FIG. 13. When such aspect is adopted, the irradiation of the therapeutic beam is suspended during the period indicated by the sign T1 referring to FIG. 13, and the time needed for such treatment may be longer. In addition, the irradiations of the therapeutic beam B and the X-ray for dynamic body tracking must be synchronized, so that it is problematic that the apparatus thereof per se becomes complex.

FIG. 14 is a time chart illustrating indicating the state of the therapeutic beam B and the irradiation of X-ray for dynamic body tracking and so forth when a flat panel detector is used for an X-ray detector instead of the image intensifier. Referring to FIG. 14, the sign B indicates ON-and-OFF of the therapeutic beam B, the sign X indicates ON-and-OFF of X-ray for dynamic body tracking and the sign R indicates the read-out state of the flat panel detector.

The flat panel detector does not equip the gate function of such as the image intensifier. In addition, the flat panel detector needs a certain time to read out the signal because of the structure in which the charge signal is accumulated in the capacitance. Therefore, referring to FIG. 14, as indicated by the broken lines, irradiation of the therapeutic beam B must be suspended not only during irradiating the X-ray for dynamic body tracking but also during the time between the read-out time 33, in which an effect of the scattered radiation S incident prior to irradiation of the X-ray for dynamic body tracking can be reset, and the signal read-out time 34 relative to the X-ray for dynamic body tracking. Therefore, the irradiation of the therapeutic beam must be suspended for the long period indicated by the sign T2 referring to FIG. 14, and the time needed for such treatment may be extremely long, accordingly. In addition, even in such case, the irradiations of the therapeutic beam B and the X-ray for dynamic body tracking must be synchronized, so that it is problematic that the apparatus thereof per se becomes complex.

The present invention is intended to solve such problems described above and the purpose of the present invention is to provide an X-ray fluoroscopy apparatus capable of performing expeditiously a treatment without suspending the irradiation of a therapeutic beam even during dynamic body tracking by an X-ray.

Means for Solving the Problem

According to the aspect of the first invention, an X-ray fluoroscopy device that is applied for a radiation therapy apparatus for performing a radiation therapy by irradiating a therapeutic beam to a subject comprises: an X-ray imaging mechanism having an X-ray tube and an X-ray detector that detects the X-ray that is irradiated from the X-ray tube and then transmits through the subject; a correction region that is formed in the X-ray detector; wherein the scattered radiation caused by irradiating the therapeutic beam to the subject can be incident, but the X-ray that is irradiated from the X-ray tube and transmits through the subject cannot be incident; and a correction element that corrects the data acquired from the region other than the correction region of the X-ray detector by applying the data acquired in the correction region.

According to aspect of the second invention, the correction region is formed in the orthogonal direction to the gate bus line relative to the X-ray detector.

According to aspect of the third invention, the correction regions are formed at both ends of the X-ray detector as a pair.

According to aspect of the fourth invention, the correction regions are formed with a filter that is installed on the surface of the X-ray detector and the scattered radiation caused by irradiating the therapeutic beam to the subject can transmit therethrough, but the X-ray that is irradiated from the X-ray tube and transmits through the subject cannot transmit therethrough.

According to aspect of the fifth invention, the correction regions are formed with X-ray irradiation region limiting members that limit the X-ray irradiation region irradiated from the X-ray tube to a part of the region on the surface of the X-ray detector.

According to aspect of the sixth invention, the correction element that corrects the data acquired in the region other than the correction region of the X-ray detector by applying a pre-measured distribution function of the scattered radiation caused by irradiating the therapeutic beam to the subject relative to the X-ray detector and the data acquired from the correction region.

According to the aspect of the seventh invention, the dynamic body tracking device for the radiation treatment comprises the X-ray fluoroscopy device according to any one of the first invention to the sixth invention.

According to the aspect of the eighth invention, the X-ray detector applicable to the X-ray fluoroscopy device according to any one of the first invention to the sixth invention comprises the correction region, wherein the scattered radiation caused by irradiating the therapeutic beam to the subject can be incident, but the X-ray that is irradiated from the X-ray tube and transmits through the subject cannot be incident.

Effect of the Invention

According to the aspects of the first invention, the seventh invention and the eight invention, the region data of the region other than the correction region is corrected by applying the data from the correction region of the X-ray detector; so that an effect of the artifact due to scattered radiation can be prevented and therefore, the irradiation of the therapeutic beam is not required to be suspended even during performing dynamic body tracking by the X-ray, so that the treatment can be performed expeditiously.

According to the aspect of the second invention, an effect of the artifact taking place in the orthogonal direction to the gate bus line relative to the X-ray detector can be prevented efficiently.

According to the aspect of the third invention, an effect of the artifact can be absolutely prevented by utilizing the pair of the correction regions formed at both ends of the X-ray detector.

According to the aspect of the fourth invention, a correction region can be formed at the X-ray detector side by utilizing a filter.

According to the aspect of the fifth invention, a correction region can be formed at the X-ray tube side by limiting the irradiation area of the X-ray.

According to the aspect of the sixth invention, an effect of the artifact can be absolutely prevented by corresponding to the distribution of the scattered radiation.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
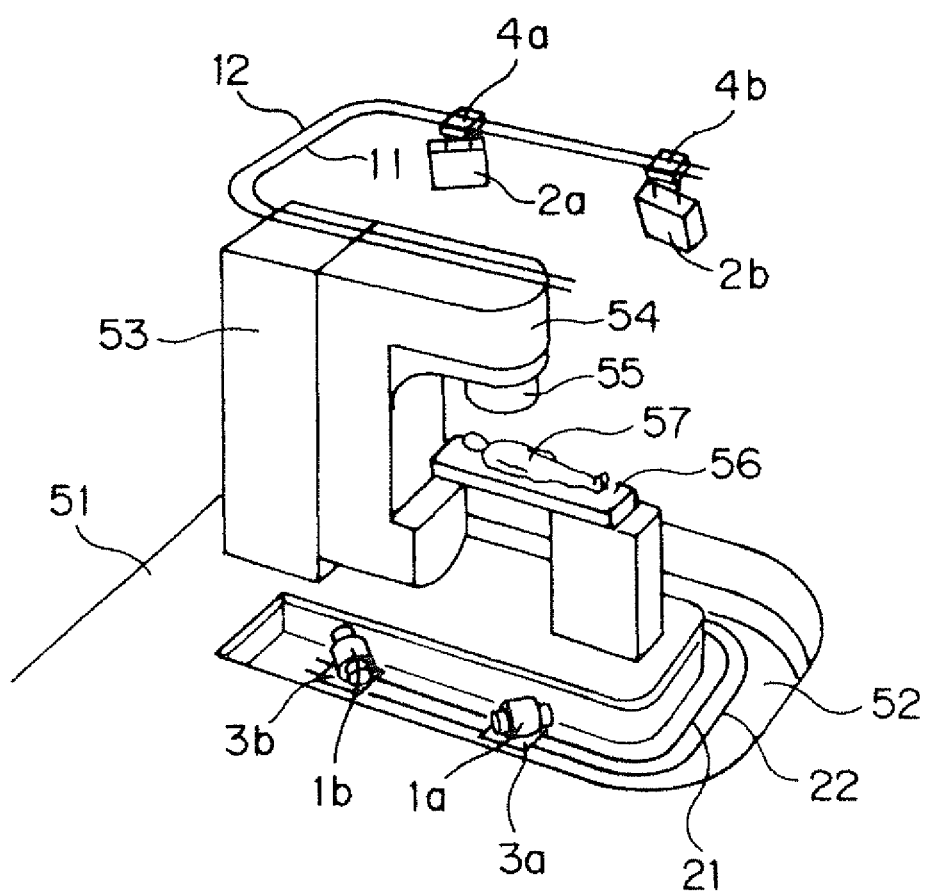
FIG. 1 is a perspective view of the radiation therapeutic apparatus applying the X-ray fluoroscopic device of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Figure 2:
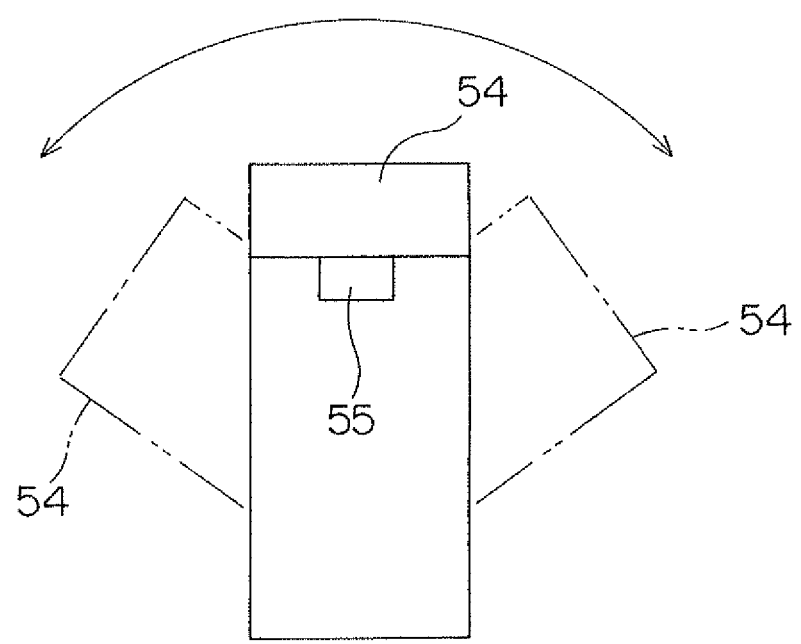
FIG. 2 is an explanatory drawing of the oscillating operation of the head 55 and the head support 54 relative to the radiation therapeutic apparatus.

The inventor sets forth Embodiments of the present invention based on the following FIGs. FIG. 1 is a perspective view of the radiation therapeutic apparatus applying the X-ray fluoroscopic device of the present invention. FIG. 2 is an explanatory drawing of the oscillating operation of the head 55 and the head support 54 relative to the radiation therapeutic device. Further, referring to FIG. 1, a pair of filters 23 described later is omitted.

The present radiation therapeutic apparatus that is to provide a therapeutic treatment by radiation of an X-ray or an electron beam to the affected area of the subject 57 lying on the table 56 comprises a gantry 53 installed on the floor 51 of the treatment room, a head support element 54 that oscillates around the axis facing the horizontal direction relative to the gantry 53 and a head 55 supported by the head support element 54 in order to irradiate the radiation to the subject 57. The head 55 is capable of irradiating the radiation to the affected area of the subject 57 from a variety of angles because of the oscillating operation of the head support element 54.

On performing a radiation therapy, the radiation must be accurately irradiated to the affected area. For such purpose, a marker is set near the affected area. The marker implanted inside the body is continuously looked at through the first X-ray fluoroscopic mechanism and the second X-ray fluoroscopic mechanism and the 3-dimensional position information as to the marker is calculated from the 2-dimensional fluoroscopic images obtained by the first X-ray fluoroscopic mechanism and the second X-ray fluoroscopic mechanism so that the marker can be structurally detected with a high degree of accuracy. In addition, a marker-less tracking in which an image of the specific region such as e.g., tumor of the subject is used instead of the marker may be used without setting the maker near the affected region of the subject.

An X-ray fluoroscopic device according to the aspect of the present invention in order to perform such fluoroscopic operation comprises: a first X-ray fluoroscopic mechanism consisting of a first X-ray tube 1a and a first flat panel detector 2a and a second X-ray fluoroscopic mechanism consisting of a second X-ray tube 1b and a second X-ray detector 2b, and further comprises the move mechanism that moves the first X-ray tube 1a and the first flat panel detector 2a to a first fluoroscopic position and a second fluoroscopic position so as to place opposite each other and also the second X-ray tube 1b and the second X-ray detector 2b to the first fluoroscopic position and the second fluoroscopic position so as to place opposite each other. According to the present X-ray fluoroscopic device, a flat panel detector is used as an X-ray detector.

In addition, referring to the following explanation and the respective figures, the first X-ray tube 1a and the second X-ray tube 1b are collectively referred as the X-ray tube 1 and the first flat panel detector 2a and the second flat panel detector 2b are collectively referred as the flat panel detector 2.

The first X-ray tube 1a is supported with the first pedestal 3a for the X-ray tube. Further, the second X-ray tube 1b is supported with the second pedestal 3b for the X-ray tube. The first rail 21 for the X-ray tube having approximately U-shape, in which two linear portions are connected with the connection element including a circular portion, and the second rail 22 for the X-ray tube having approximately U-shape as the same as the first rail 21 for the X-ray tube, in which two linear portions are connected with the connection element including a circular portion, are installed on the bottom surface 52 of the concave portion formed on the floor 51 in the imaging room. The first rail 21 and the second rail 22 for the X-ray tube for such X-ray tubes are parallel in-place each other. Then, the first pedestal 3a for the X-ray tube and the second pedestal 3b for the X-ray tube move to the first fluoroscopy position and the second fluoroscopy position, as described later, by guiding with the first rail 21 and the second rail 22.

Also, the flat panel detector 2a is supported by the first pedestal 4a for the flat panel detector. Also, the flat panel detector 2b is supported by the first pedestal 4b for the flat panel detector. The first rail 11 for the flat panel detector having approximately U-shape, in which two linear portions are connected with the connection element including a circular portion, and the second rail 12 for the flat panel detector having approximately U-shape as the same as the first rail 11 for the flat panel detector, in which two linear portions are connected with the connection element including a circular portion, are suspended from the ceiling of the imaging room. Such first rail 11 for the flat panel detector and the second rail 12 for the flat panel detector are parallel in-place each other. Then, the first pedestal 4a for the flat panel detector and the second pedestal 4b for the flat panel detector move to the first fluoroscopy position and the second fluoroscopy position by being guided by the first rail 11 and the second rail 12.

Figure 3:
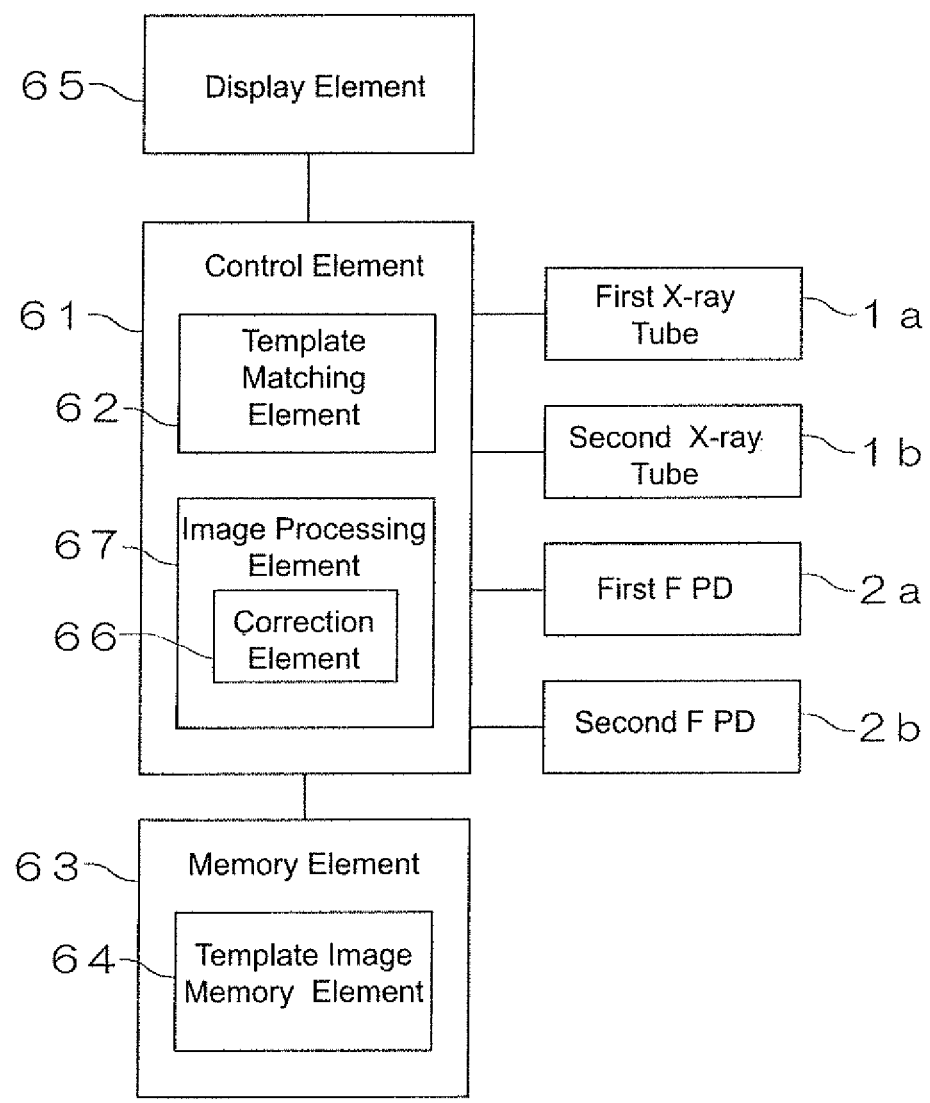
FIG. 3 is a block diagram illustrating the main control system of the X-ray fluoroscopic device of the present invention.

FIG. 3 is a block diagram illustrating the main control system of the X-ray fluoroscopic device according to the aspect of the present invention.

Such X-ray fluoroscopic device includes a control element 61 to control the entire device. Such control element 61 comprises the template matching element 62 that specifies in real-time the position of the marker or the specific tumor region relative to the images of the subject 57 imaged every constant time, by performing template matching utilizing the template image relative to the images of the subject 57, continuously imaged every constant time. In addition, such control element 61, as described later, comprises an image processing element 67 having the correction element 66 in order to correct the data of the region other than the correction region by applying the data of the correction region. In addition, the control element 61 is connected to a display element 65 consisting of the liquid crystal display panel and so forth to display the fluoroscopic image. Further, the control element 61 is also connected to the memory element 63. The memory element 63 includes the template image memory element 64.

The control element 61 is connected, as described above, to the first X-ray tube 1a, the second X-ray tube 1b, the flat panel detector 2a and the second flat panel detector 2b. Further the control element 61 is connected to a driving element, not shown in FIG., as described above, to drive the first pedestal 3a for the X-ray tube, the second pedestal 3b for the X-ray tube, the first pedestal 4a for the flat panel detector, and the second pedestal 4b for the flat panel detector. Further, the control element 61 is also connected to the radiation therapeutic apparatus referring to FIG. 1.

According to the X-ray fluoroscopic device of the present invention, first of all, the template corresponding to the marker or the specific location of e.g. a tumor and so forth is prepared for the template matching. In such case, the first X-ray tube 1a and the first flat panel detector 2a or the second X-ray tube 1b and the second flat panel detector 2b are in-place facing each other by moving the first X-ray tube 1a, the second X-ray tube 1b, the flat panel detector 2a, and the second flat panel detector 2b to the first fluoroscopy position and the second fluoroscopy position. And an image including the marker or the specific location is imaged by continuously imaging the subject 57.

And when the treatment is performed on subject 57, the marker or the location of the specific region is detected by the X-ray fluoroscopic device according to the aspect of the present invention. At this time, the fluoroscopy is conducted at the frame rate around 30 fps relative to the region including the marker M or the specific region. Then, referring to FIG. 3, the template matching element 62 performs the template matching by utilizing the template image stored in the template image memory element 64 relative to the region including the marker M or the specific region imaged every constant time. Specifically, the template image is matched relative to the region including the marker or the specific region imaged every constant time.

And it is determined that the matching is successful when the matching result is beyond the pre-set threshold value for the matching. And then the location of the marker or the specific region can be identified. And the position of the radiation to be irradiated relative to the affected area of the subject 57 can be adjusted based on the location of such marker or the specific region.

Figure 12:
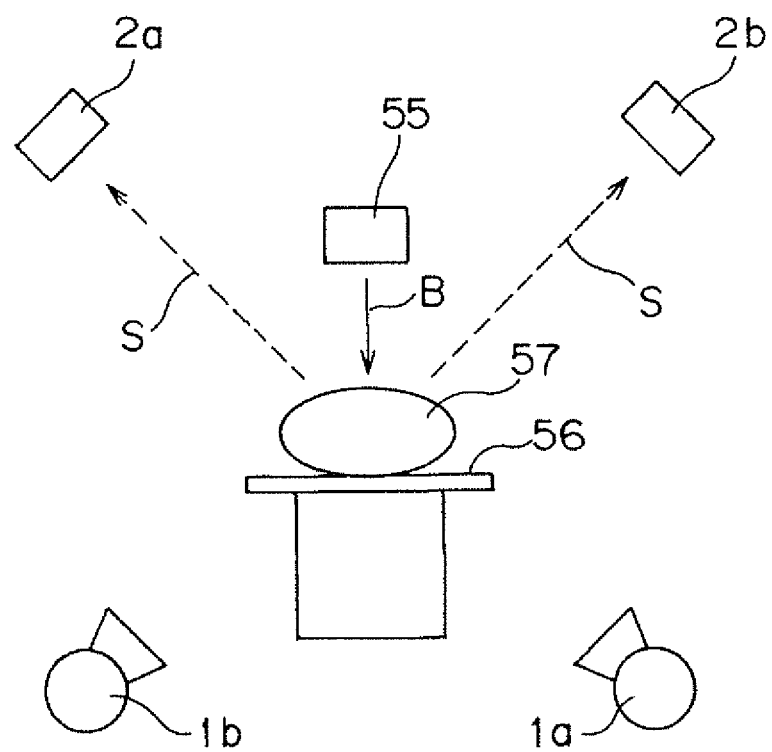
FIG. 12 is a schematic view illustrating the state in which a radiation therapy is being conducted by a radiation therapeutic apparatus having a traditional fluoroscopic device.
Figure 13:
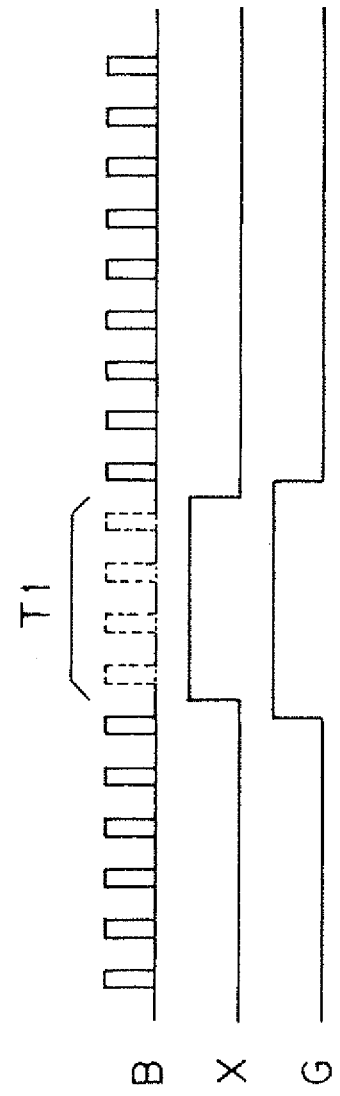
FIG. 13 is a timing chart illustrating the state of the therapeutic beam B and the irradiation of an X-ray for dynamic body tracking and so forth when the image intensifier (I. I.) is applied for an X-ray detector.
Figure 14:
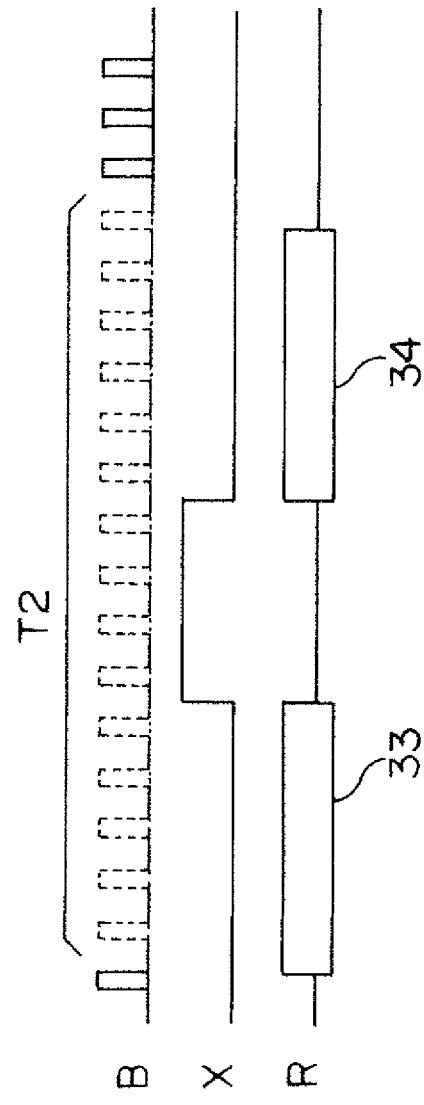
FIG. 14 is a timing chart illustrating the state of the therapeutic beam B and the irradiation of X-ray for dynamic body tracking and so forth when a flat panel detector is used for an X-ray detector. *

According to the aspect of such X-ray fluoroscopic device, the therapeutic beam B after irradiated from the head 55 to the subject 57 becomes scattered radiation S and is incident into the first flat panel detector 2a and the second flat panel detector 2b as well as the conventional apparatus having an X-ray fluoroscopic device referring to FIG. 12. When such scattered radiation S are incident into the first flat panel detector 2a and the second flat panel detector 2b, an artifact takes place in the image imaged by the first flat panel detector 2a and the second flat panel detector 2b, so that it is problematic that the dynamic body tracking can be interrupted. At this time, the flat panel detector 2 is used as the X-ray detector, an irregular line particularly in the orthogonal direction to the gate bus line at the flat panel detector 2 may takes place easily. Because the flat panel detector 2 structure-wise reads out the charge signal, accumulated in the capacitance, in order every gate bus line. Then, the irradiation of the therapeutic beam must be suspended during the long period indicated by the sign T2 referring to FIG. 14 in order to prevent an occurrence of the artifact in the flat panel detector 2, and the time needed for such treatment may be extremely long, accordingly.

Therefore, according to the X-ray fluoroscopic device of the present invention, a pair of correction regions, in which the scattered line can be incident but the X-ray transmitted through the subject cannot be incident, are formed at both ends of the flat panel detector 2 and the data from the correction region is used to correct the value detected from the region other than the correction region.

Figure 4:
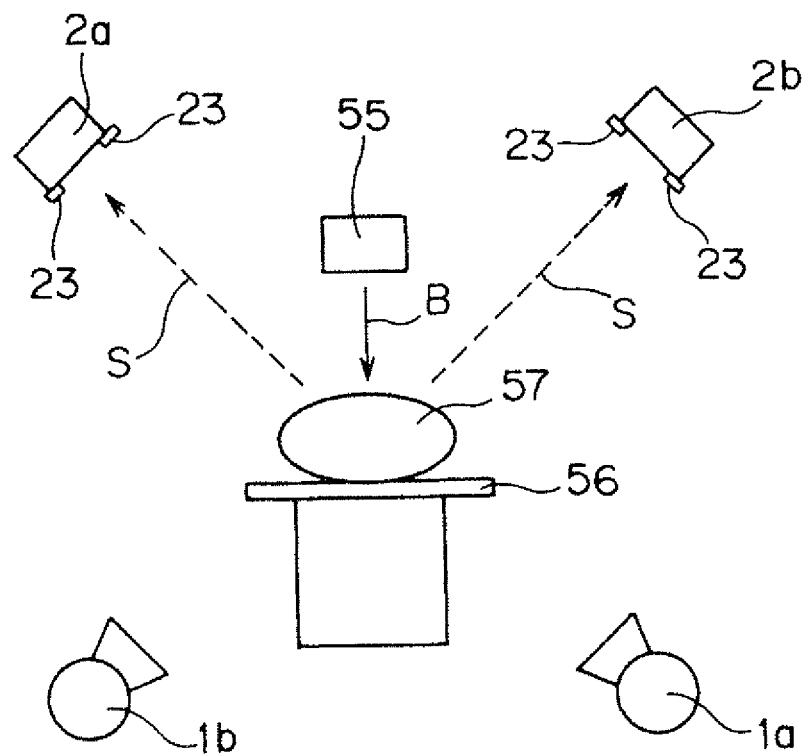
FIG. 4 is a schematic view illustrating the state in which a radiation therapy is being conducted by a radiation therapeutic device having an X-ray fluoroscopic device according to the aspect of the Embodiment 1.

FIG. 4 is a schematic view illustrating the state in which a radiation therapy is being performed by a radiation therapeutic apparatus having an X-ray fluoroscopic device according to the aspect of the Embodiment 1 of the present invention. In addition, FIG. 5 is a front view illustrating a pair of filters 23 arranged on the surface of the flat panel detector 2.

Referring to FIG. 1 and as described above, such present radiation therapeutic device is to provide an therapeutic treatment by irradiating an X-ray or an electron beam to the affected area of the subject 57 lying on the imaging table 56 and a head 55 that irradiates the therapeutic beam B to the subject 57. In addition, referring to FIG. 1 and as described above, such radiation therapeutic apparatus comprises: a first X-ray fluoroscopic mechanism consisting of the first X-ray tube 1*a* and the first flat panel detector 2*a;* and a second X-ray fluoroscopic mechanism consisting of the second X-ray tube 1*b* and the second flat panel detector 2*b*, in order to fluoroscope an image including the marker inside the subject 57 in order to perform a dynamic body tracking.

According to the aspect of such radiation therapy apparatus, the therapeutic beam B after irradiated from the head 55 to the subject 57 becomes scattered radiation S incident into the first flat panel detector 2*a* and the second flat panel detector 2*b* as well as the radiation therapy apparatus having the conventional X-ray fluoroscopic device referring to FIG. 12. When such scattered radiation S are incident into the first flat panel detector 2*a* and the second flat panel detector 2*b*, an artifact takes place in the image imaged by the first flat panel detector 2*a* and the second flat panel detector 2*b*, so that it is problematic that the dynamic body tracking can be interrupted.

Figure 5:
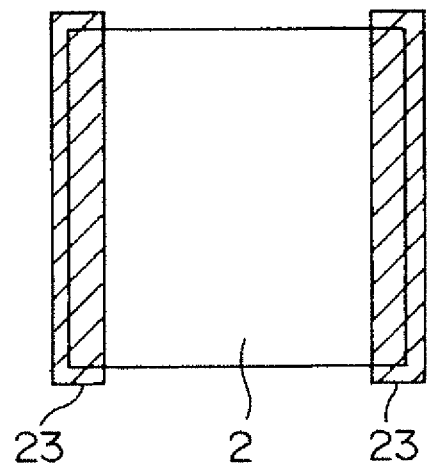
FIG. 5 is a front view illustrating a pair of filters 23 arranged on the surface of the flat panel detector 2.

Therefore, referring to FIG. 5, according to the aspect of such radiation therapy apparatus, a pair of filters 23 are installed at both ends of the surface (subject 57 side) of the flat panel detector 2. Such filters 23 transmit the scattered radiation S caused by irradiating the therapeutic beam to the subject 57 therethrough, but the X-ray that is irradiated from the X-ray tube 1 and transmits through the subject 57 cannot transmit therethrough property-wise. Such filters 23 can be a thin board made of tungsten or lead.

In addition, such pair of filters 23 is arranged in the orthogonal direction to the gate bus line relative to the flat panel detector 2 as described later. Accordingly, both ends orthogonal to the gate bus line relative to the flat panel detector 2 are covered by the pair of filters. And according to an effect due to such pair of filters 23, correction regions; in which the scattered radiation S caused by irradiating the therapeutic beam to the subject 57 can be incident, but the X-ray that is irradiated from the X-ray tube 1 and transmits through the subject 57 cannot be incident; are formed in the orthogonal direction to the gate bus line relative to the flat panel detector 2.

Figure 6:
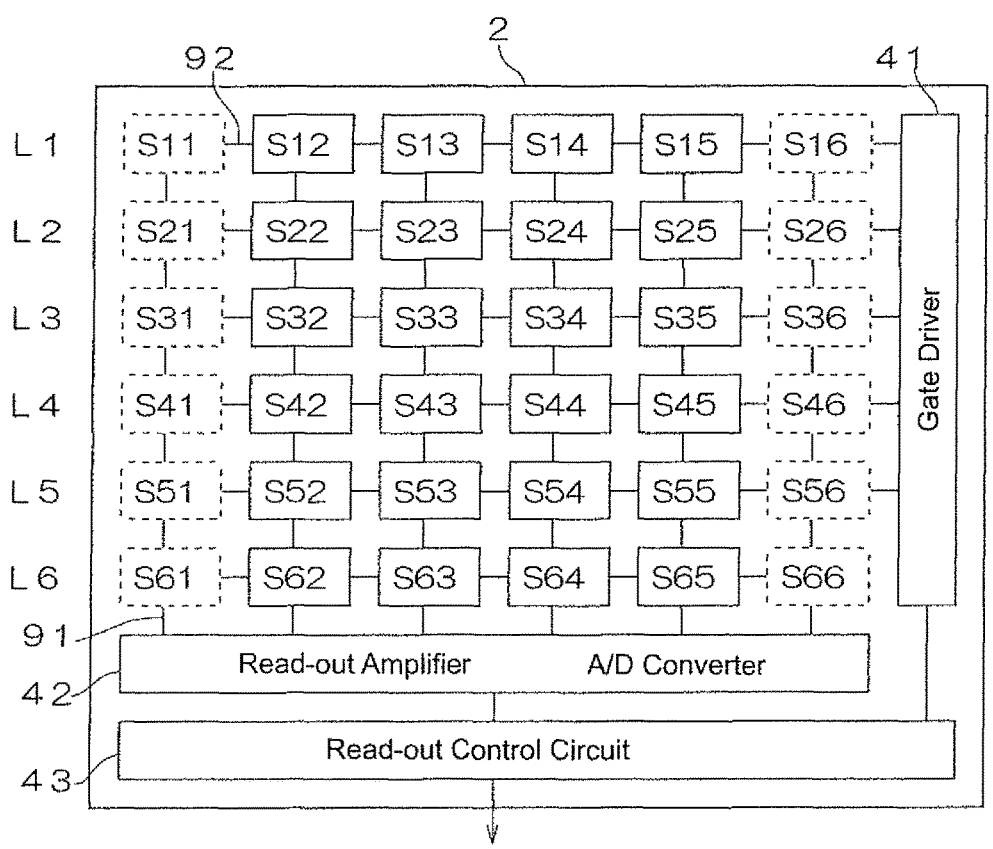
FIG. 6 is an explanatory drawing illustrating the schematic structure of the flat panel detector 2 and so forth.

FIG. 6 is an explanatory drawing illustrating the schematic structure of the flat panel detector 2 and so forth.

Referring to FIG. 6, the flat panel detector 2 having 36 pixels, i.e., 6 rows by 6 columns, is schematically illustrated. A practical flat panel detector 2 has pixels consisting of e.g., 1024 rows by 1024 columns.

Referring to FIG. 6, the signs L1-L6 indicate the rows consisting of pixels along the gate bus line 92. Referring to FIG. 6, the row L1 extending in the right-and-left direction consists of 6 pixels of S11, S12, S13, S14, S15 and S16. Other lines L2, L3, L4, L5 and L6 have the same aspect. An X-ray signal incident into the flat panel detector 2 is read-out as L1, L2, L3, L4, L5 and L6 in order. Therefore, an irregular line in the orthogonal direction to the gate bus line 92 takes place in the flat panel detector 2 due to difference between read-out times.

In addition, referring to FIG. 6, the sign 91 indicates the data bus line consisting of 6 columns extending in the up-and-down direction of FIG. 6. And, according to the aspect of the present Embodiment, the column consisting of pixels S11, S21, S31, S41, S51 and S61 and the column consisting of S16, S26, S36, S46, S56 and S66 covered by the filters 23 referring to FIG. 4 and FIG. 5 make the correction regions, in which the scattered radiation S caused by irradiating the therapeutic beam B to the subject 57 can be incident, but the X-ray that is irradiated from the X-ray tube 1 and transmits through the subject cannot be incident.

In addition, such flat panel detector 2 comprises a gate driver 41, a read-out amplifier, an A/D converter 42 and a read-out control circuit 43.

Figure 7:
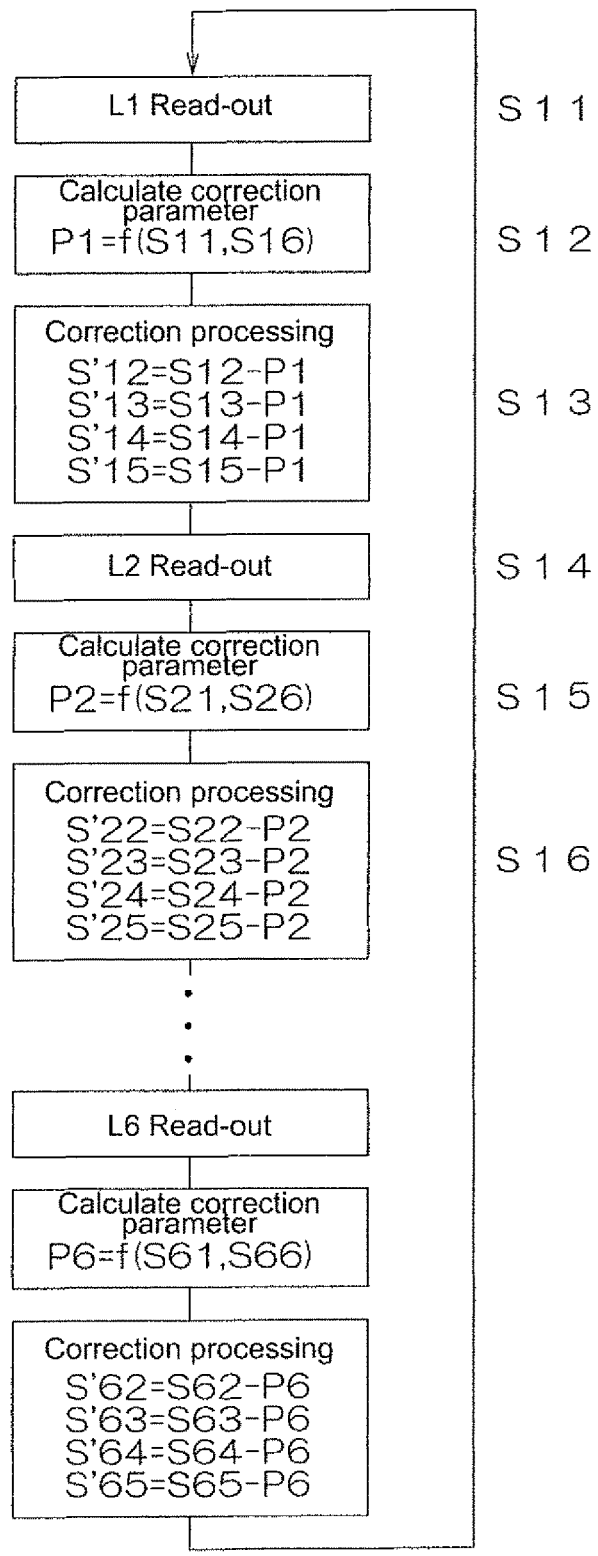
FIG. 7 is a flow-chart illustrating the detection operation of the X-ray relative to the X-ray fluoroscopic device according to the aspect of the Embodiment 1.

Next, the inventor set forth a detection operation for X-ray relative to the X-ray fluoroscopic device. FIG. 7 is a flowchart illustrating the detection operation for the X-ray relative to the X-ray fluoroscopic device according to the aspect of the Embodiment 1.

First, when the flat panel detector 2 detects an X-ray according to the X-ray fluoroscopic device of the present invention, the pixel value of each pixel S11, S12, S13, S14, S15 and S16 of the row L1 is read out (Step S11).

Next, a correction parameter P1 is calculated from the pixel value of the pixel S11 and the pixel S16 arranged in the correction region by using the function f(S11, S16) (Step S12). Referring to FIG. 3, such calculation of the parameter P1 is executed by the correction element 66 in the image processing element 67. An averaging processing, in which the pixel value of S11 and the pixel value of S16 are added and the sum thereof is divided by 2, can be applied as such function f(S11, S16). A function other than the averaging processing can be also applied as the function f(S11, S16).

Next, a correction processing is executed (Step S13). Such correction processing is a step of correcting the pixel values of the pixel S12, S13, S14 and S15 arranged in the region other than the correction region by using the correction parameter P1. According to the aspect of the present Embodiment, the corrected pixel value S'12, S'13, S'14 and S'15 is obtained by subtracting the correction parameter P1 from the pixel values of the pixel S12, S13, S14 and S15 arranged in the region other than the correction region. Referring to FIG. 3, such correction processing is executed by the correction element 66 in the image processing element 67.

Next, the pixel value of each pixel S21, S22, S23, S24, S25 and S26 of the row L2 is read out (Step S14).

Next, an correction parameter P2 is calculated from the pixel value of the pixel S21 and the pixel S26 arranged in the correction region by using the function f(S21, S26) (Step S15). Referring to FIG. 3, such calculation of the parameter P2 is also executed by the correction element 66 in the image processing element 67.

Next, a correction processing is executed (Step S16). Such correction processing is a step of correcting the pixel values of the pixel S22, S23, S24 and S55 arranged in the region other than the correction region by using the correction parameter P2. Specifically, the corrected pixel value S'22, S'23, S'24 and S'25 is obtained by subtracting the correction parameter P2 from the pixel values of the pixel S22, S23, S24 and S25 arranged in the region other than the correction region. Referring to FIG. 3, such correction processing is also executed by the correction element 66 in the image processing element 67.

The above operation is executed until the row L6 as well. And while the flat panel detector 2 is detecting the X-ray, the same operation is repeated.

Figure 8:
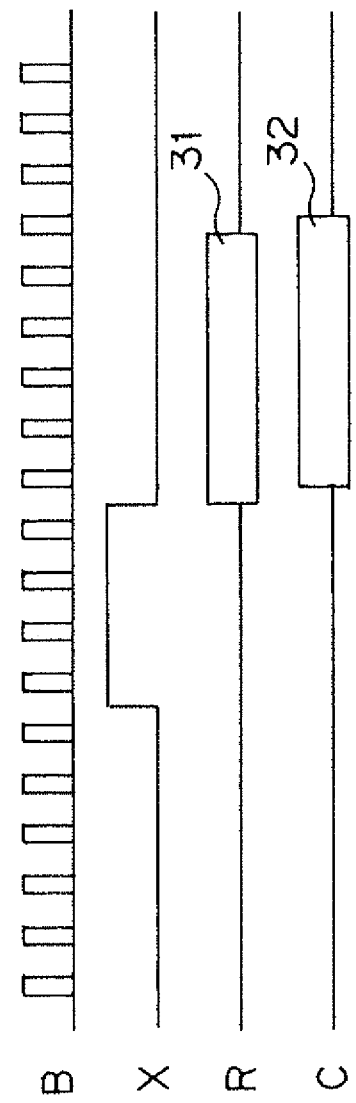
FIG. 8 is a timing chart illustrating the state of the therapeutic beam B and the irradiation of an X-ray for dynamic body tracking and so forth relative to the X-ray fluoroscopic device according to the present invention.

FIG. 8 is a timing chart illustrating the state of the therapeutic beam 13 and the irradiation of an X-ray for dynamic body tracking and so forth relative to the X-ray fluoroscopic device according to the present invention. Referring to FIG. 8, the sign B indicates ON-and-OFF of the therapeutic beam B, the sign X indicates ON-and-OFF of an X-ray for dynamic body tracking, the sign R indicates the read-out state of the flat panel detector 2 and the sign C indicates the state in which the above correction processing is being executed.

Referring to FIG. 8, when the X-ray fluoroscopic device of the present invention is used, the therapeutic beam B can be continuously irradiated while read-out of the pixel value in the flat panel detector 2 and correction thereof are being executed in series following irradiation of the X-ray for dynamic body tracking. In such way, the irradiation of the therapeutic beam B is not required to be suspended, so that not only the time needed for the treatment can be shorten, but also synchronization between the therapeutic beam B and the X-ray for dynamic body tracking is no longer mandatory, and therefore a simple apparatus system can be effective.

Figure 9:
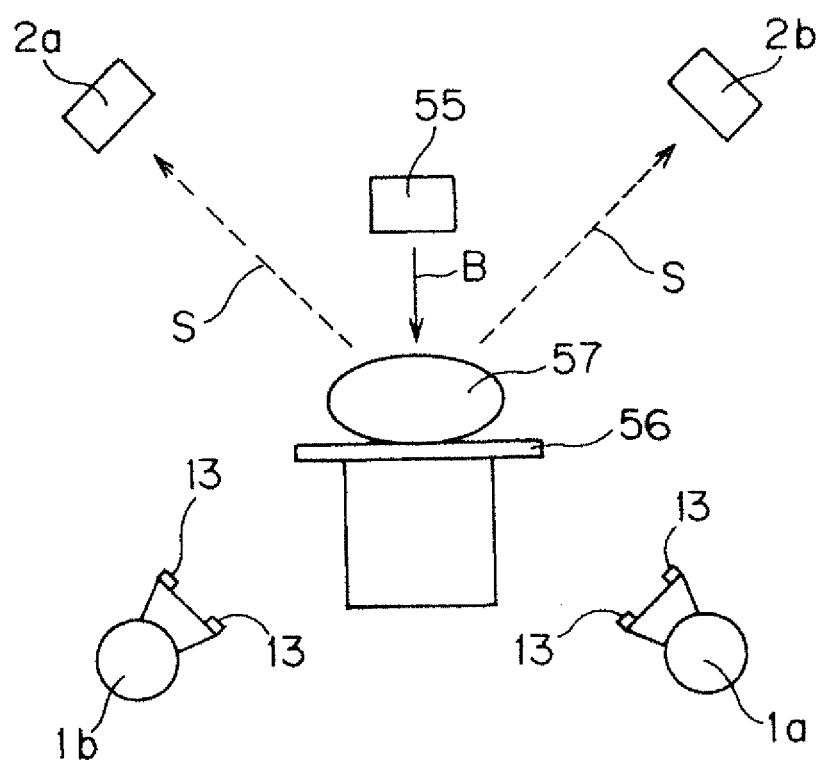
FIG. 9 is a schematic view illustrating the state in which a radiation therapy is being conducted by a radiation therapeutic apparatus having the X-ray fluoroscopic device according to the aspect of the Embodiment 2.
Figure 10:
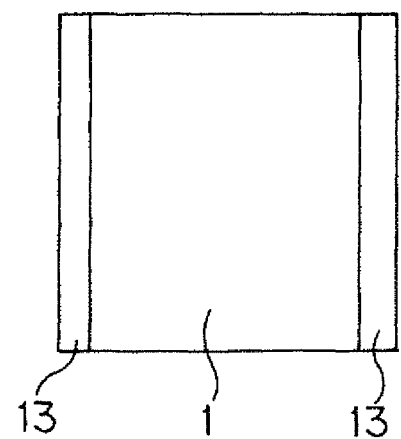
FIG. 10 is a front view illustrating a pair of X-ray irradiation region limiting members 13 arranged on the surface of the X-ray tube 1.

Next, the inventors set forth another Embodiment of the present invention. FIG. 9 is a schematic view illustrating the state in which a radiation therapy is being performed by an radiation therapeutic apparatus having an X-ray fluoroscopic device according to the aspect of the Embodiment 2 of the present invention. FIG. 10 is a front view illustrating a pair of X-ray irradiation region limiting members 13 arranged on the surface of the X-ray tube 1.

According to the aspect of the Embodiment 1 as described above, the pair of the filters 23, which is installed on the surface of the flat panel detector 2, allows the scattered radiation S caused by irradiation of the therapeutic beam B to the subject 57 to transmit but allows the X-ray that is irradiated from the X-ray tube 1 and transmitting the subject 57 not to transmit as the correction region forming means to form the correction region in the flat panel detector 2, in which the scattered radiation S caused by irradiation of the therapeutic beam B to the subject 57 can be incident but the X-ray that is irradiated from the X-ray tube 1 and transmitting the subject 57 cannot be incident. In contrast, referring to FIG. 9 and FIG. 10, according to the aspect of the Embodiment 2, a pair of the X-ray irradiation region limiting members 13 to limit the irradiation region of the X-ray irradiated from the X-ray tube 1 to a region that is a part of the surface of the flat panel detector 2 is applied.

An X-ray blocking member, e. g., a thin lead plate and so forth, can be applied for such pair of the X-ray irradiation region limiting members 13. More common material can be used as such X-ray irradiation region limiting members 13.

Such pair of the X-ray irradiation region limiting members 13 is arranged in the orthogonal direction to the gate bus line relative to the flat panel detector 2. And according to an operation with such pair of X-ray irradiation region limiting members 13, correction regions; in which the scattered radiation S caused by irradiating the therapeutic beam to the subject 57 therethrough can be incident in both ends of the flat panel detector 2, but the X-ray that is irradiated from the X-ray tube I and transmits through the subject 57 cannot be incident; are formed in the orthogonal direction to the gate bus line relative to the flat panel detector 2.

With regard to the X-ray fluoroscopic device according to the aspect of the Embodiment 2, as well as the X-ray fluoroscopic device according to the aspect of the Embodiment 1, the therapeutic beam B can be continuously irradiated while reading-out the pixel value in the flat panel detector 2 and correction thereof are being executed in series following irradiation of the X-ray for dynamic body tracking. In such way, the irradiation of the therapeutic beam B is not required to be suspended, so that not only the time needed for the treatment can be shorten, but also synchronization between the therapeutic beam B and the X-ray for dynamic body tracking is no longer mandatory, and therefore a simple apparatus system can be effective.

Figure 11:
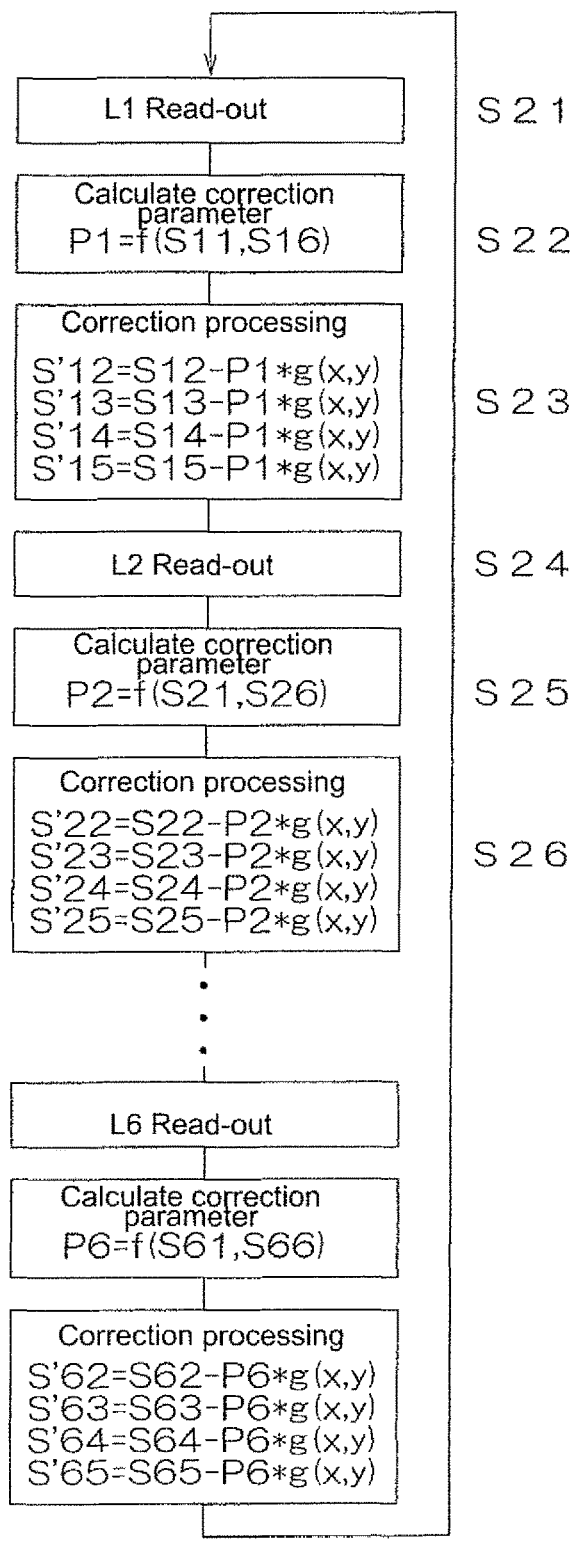
FIG. 11 is a flow-chart illustrating the X-ray detection operation according to the aspect of the other Embodiment.

Next, the inventors set forth the other aspect of the Embodiment relative to the X-ray detection operation with regard to the X-ray fluoroscopic device according to the aspects of the Embodiment 1 and the Embodiment 2 as described above. FIG. 11 is a flow-chart illustrating the X-ray detection operation according to the aspect of the other Embodiment.

Referring to FIG. 7, relative to the X-ray detection operation with regard to the X-ray fluoroscopic device, the correction parameter P1 is calculated from the pixel value of the pixel S11 and the pixel S16 arranged in the correction region by using the function f(S11, S16). On the other hand, with regard to the X-ray detection operation according to the aspect of the present Embodiment, the correction parameter P1 is calculated by using a pre-measured distribution function of the scattered radiation S caused by irradiating the therapeutic beam B to the subject 57 relative to the flat panel detector 2 in addition to using the function f(S11, S16).

When such X-ray detection operation is executed, a distribution function of the scattered radiation S caused by irradiating the therapeutic beam B to the subject 57 relative to the flat panel detector 2 is experimentally acquired in advance. Such distribution function is stored in e.g., a memory element 63 referring to FIG. 3. And, when the correction parameter P1 is calculated, such distribution function is read out.

According to the X-ray fluoroscopic device of the present Embodiment, when the flat panel detector 2 detects an X-ray, firstly, the pixel value of each pixel S11, S12, S13, S14, S15 and S16 of the row L1 is read out (Step S21).

Next, a correction parameter P1 is calculated from the pixel value of the pixel S11 and the pixel S16 arranged in the correction region by using the function f(S11, S16) (Step S22). Referring to FIG. 3, such calculation of the parameter P1 is executed by the correction element 66 in the image processing element 67. An averaging processing, in which the pixel value of S1 and the pixel value of S16 are added and the sum thereof is divided by 2, and so forth can be applied as such function f(S11, S16).

Next, a correction processing is executed (Step S23). Such correction processing is a step of correcting the pixel values of S12, S13, S14 and S15 arranged in the region other than the correction region by using the correction parameter P1 and the distribution function g(x, y) of the scattered radiation S caused by irradiating the therapeutic beam B to the subject 57 in the plan of the flat panel detector 2 relative to the flat panel detector 2, wherein such distribution function g(x, y) is experimentally acquired in advance. According to the aspect of the present Embodiment, following multiplying the distribution function g(x, y) of the scattered radiation S by the correction parameter P1, the corrected pixel values S'12, S'13, S'14 and S'15 are obtained by subtracting the multiplication value following multiplication from the pixel values of the pixels S12, S13, S14 and S15 arranged in the region other than the correction region. Referring to FIG. 3, such correction processing is executed by the correction element 66 in the image processing element 67.

Next, the pixel value of each pixel S21, S22, S23, S24, S25 and S26 of the row L2 is read out (Step S24).

Next, a correction parameter P2 is calculated from the pixel value of the pixel S21 and the pixel S26 arranged in the correction region by using the function f(S21, S26) (Step S25). Referring to FIG. 3, such calculation of the parameter P2 is also executed by the correction element 66 in the image processing element 67.

Next, a correction processing is executed (Step S26). Even in such correction processing, the pixel values of the pixel S22, S23, S24 and S25 arranged in the region other than the correction region are corrected by using the multiplication value that is obtained by multiplying the distribution function g(x, y) of the scattered radiation S by the correction parameter P2. Specifically, the corrected pixel value S'22, S'23, S'24 and S'25 is obtained by subtracting the multiplication value, which is obtained by multiplying the distribution function g(x, y) of the scattered radiation S by the correction parameter P2, from the pixel values of the pixel S22, S23, S24 and S25 arranged in the region other than the correction region. Referring to FIG. 3, such correction processing is also executed by the correction element 66 in the image processing element 67.

The above operation is executed until the row L6 as well. And while the flat panel detector 2 is detecting the X-ray, the same operation is repeated.

Further, according to the aspect of the Embodiments as described above, the first rail 11 and the second rail 12 for the flat panel detector and the first rail 21 and the second rail 22 for the X-ray tube have approximately U-shape, but such shape can be an arc-shape.

Further, according to the aspect of any Embodiments as described above, the pair of correction regions are installed at both ends of the flat panel detector 2, but the correction region can be installed just one end of the flat panel detector 2.

REFERENCE OF SIGN

1a First X-ray tube
1b Second X-ray tube
2a First flat panel detector
2b Second flat panel detector
3a First pedestal for X-ray tube
3b Second pedestal for X-ray tube
4a first pedestal for flat panel detector
4b Second pedestal for flat panel detector
11 First rail
12 Second rail
21 Third rail
22 Fourth rail
13 X-ray irradiation region limiting member
23 Filter
53 Gantry
54 Head support element
55 Head
56 Table
57 Subject
61 Control element
63 Memory element
66 Correction element
67 Image processing element
91 Data bus line
92 Gate bus line Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray fluoroscopic device that is used for a radiation therapy apparatus to perform a radiation therapy by irradiating a therapeutic beam to a subject, comprising:
    an X-ray imaging mechanism having an X-ray tube and an X-ray detector that detects an X-ray that is irradiated from the X-ray tube and then transmits through the subject;
    a correction region of said X-ray detector;
        wherein a scattered radiation caused by irradiating said therapeutic beam to said subject can be incident therein, but the X-ray that is irradiated from said X-ray tube and transmits through the subject cannot be incident therein; and
    a correction element that corrects data acquired from a region other than the correction region of the X-ray detector by applying the data acquired from the correction region.

2. The X-ray fluoroscopic device according to claim 1, wherein:
    said correction region is formed in the orthogonal direction to the gate bus line of said X-ray detector.

3. The X-ray fluoroscopic device according to claim 1, wherein:
    said correction regions are formed at both ends of said X-ray detector as a pair.

4. The X-ray fluoroscopic device according to claim 1, wherein:
    said correction region is formed with a filter that is installed on a surface of the X-ray detector; and the scattered radiation caused by irradiating the therapeutic beam to the subject can transmit therethrough, but the X-ray that is irradiated from the X-ray tube and transmits through the subject cannot transmit therethrough.

5. The X-ray fluoroscopic device according to claim 1, wherein:
    said correction region is formed with an X-ray irradiation region limiting member that limits the X-ray irradiation region irradiated from said X-ray tube to a part of said region on the surface of said X-ray detector.

6. The X-ray fluoroscopic device according to claim 1, wherein:
    said correction region corrects the data acquired from the region other than said correction region of said X-ray detector by applying a pre-measured distribution function of the scattered radiation caused by irradiating said therapeutic beam to said subject relative to said X-ray detector and the data acquired by said correction region.

7. A dynamic body tracking apparatus for a radiation therapy comprising:
    an X-ray fluoroscopic device according to claim 1.

8. An X-ray detector, for an X-ray fluoroscopic device according to claim 1, used for a radiation therapy apparatus to perform a radiation therapy by irradiating a therapeutic X-ray beam to a subject, the X-ray detector comprising:
    an X-ray detector correction region on said X-ray detector; and
    wherein a scattered radiation caused by irradiating said therapeutic X-ray beam to said subject can be incident on said X-ray detector correction region, but said therapeutic X-ray beam that is irradiated from an X-ray tube and transmits through the subject cannot be incident on said X-ray detector correction region.

* * * * *